(12) United States Patent
De Jong (10) Patent No.: US 9,730,652 B2
(45) Date of Patent: Aug. 15, 2017

(54) DEVICE AND METHOD FOR RADIOGRAPHIC AND NUCLEAR IMAGING OF AN OBJECT

(71) Applicant: UMC Utrecht Holding B.V., Utrecht (NL)

(72) Inventor: Hugo Wilhelmus Antonius Maria De Jong, Zeist (NL)

(73) Assignee: UMC UTRECHT HOLDING B.V., Utrecht (NL)

( * ) Notice: Subject to any disclaimer, the term of this patent is extended or adjusted under 35 U.S.C. 154(b) by 12 days.

(21) Appl. No.: 14/652,057

(22) PCT Filed: Dec. 12, 2013

(86) PCT No.: PCT/NL2013/050898
§ 371 (c)(1),
(2) Date: Jun. 12, 2015

(87) PCT Pub. No.: WO2014/092574
PCT Pub. Date: Jun. 19, 2014

(65) Prior Publication Data
US 2015/0320375 A1 Nov. 12, 2015

(30) Foreign Application Priority Data
Dec. 13, 2012 (NL) .................................. 2009981

(51) Int. Cl.
*G01N 23/04* (2006.01)
*A61B 6/03* (2006.01)
(Continued)

(52) U.S. Cl.
CPC .............. *A61B 6/032* (2013.01); *A61B 6/037* (2013.01); *A61B 6/4258* (2013.01);
(Continued)

(58) Field of Classification Search
None
See application file for complete search history.

(56) References Cited

U.S. PATENT DOCUMENTS 7,149,565 B2 * 12/2006 Kojima ................. A61B 6/032
250/363.03
2003/0012331 A1 * 1/2003 Kojima ................. A61B 6/037
378/4
(Continued)

FOREIGN PATENT DOCUMENTS

IL   WO 0075691 A1 * 12/2000 ............. A61B 6/032
JP   2013215523 A * 10/2013
(Continued)

*Primary Examiner* — Andrew Smyth
(74) *Attorney, Agent, or Firm* — Birch, Stewart, Kolasch & Birch, LLP (57) ABSTRACT

A method and device, e.g. a C-arm device, for radiographic and nuclear imaging of an object by means of x-ray and gamma emission imaging. The device comprises a support installation with opposed first and second support members, wherein an x-ray source is mounted on the first support member and an x-ray detector on the second support member. The first support member is additionally provided with at least two gamma cameras that are each located adjacent the x-ray source. Each of said at least two gamma cameras comprising a collimator with one or more collimator openings and a gamma radiation detector. Each of the at least two gamma cameras has an associated field of view. The fields of view of the gamma cameras overlap partly, said overlap defining a focus volume that is seen by the at least two gamma cameras. The focus volume is located between the x-ray source and the x-ray detector so that the x-ray beam passes through the focus volume and the focus volume F is seen by the x-ray detector. The x-ray source, x-ray detector, and gamma cameras are maintained in a stationary acquisition position during x-ray and gamma image data acquisition (Continued)

of x-ray and gamma radiation images respectively, which images are fused into a fused image.

12 Claims, 8 Drawing Sheets

(51) Int. Cl.
  *A61B 6/00* (2006.01)
  *A61B 6/12* (2006.01)
(52) U.S. Cl.
  CPC .......... *A61B 6/4291* (2013.01); *A61B 6/4417* (2013.01); *A61B 6/4441* (2013.01); *A61B 6/5235* (2013.01); *A61B 6/5247* (2013.01); *A61B 6/12* (2013.01)

(56) References Cited

U.S. PATENT DOCUMENTS

| | | | | |
|---|---|---|---|---|
| 2003/0108147 A1* | 6/2003 | Kojima | ................ | A61B 6/4241 378/19 |
| 2003/0118155 A1* | 6/2003 | Ueno | ................ | A61B 6/032 378/177 |
| 2003/0153828 A1* | 8/2003 | Kojima | ................ | A61B 6/032 600/425 |
| 2003/0179853 A1* | 9/2003 | Amemiya | ................ | A61B 6/037 378/63 |
| 2004/0179651 A1* | 9/2004 | Tong | ................ | A61B 6/00 378/98.8 |
| 2004/0190676 A1* | 9/2004 | Kojima | ................ | G01N 23/046 378/19 |
| 2005/0023471 A1* | 2/2005 | Wang | ................ | A61B 6/032 250/363.04 |
| 2005/0207526 A1* | 9/2005 | Altman | ................ | A61B 6/032 378/20 |
| 2006/0084961 A1* | 4/2006 | Kadziauskas | .. | A61B 17/320068 606/15 |
| 2006/0086905 A1* | 4/2006 | Fritzler | ................ | G01T 1/2985 250/363.05 |
| 2007/0085011 A1* | 4/2007 | Ritter | ................ | A61B 6/4441 250/363.05 |
| 2007/0102645 A1* | 5/2007 | Maschke | ................ | G01T 1/1615 250/370.09 |
| 2007/0228283 A1* | 10/2007 | Graumann | ................ | G01T 1/2985 250/363.05 |
| 2007/0232881 A1* | 10/2007 | Shai | ................ | A61B 6/0457 600/407 |
| 2008/0084961 A1* | 4/2008 | Keppel | ................ | A61B 6/0414 378/37 |
| 2009/0252287 A1* | 10/2009 | Boese | ................ | A61B 6/02 378/17 |
| 2012/0265050 A1* | 10/2012 | Wang | ................ | A61B 5/055 600/411 |

FOREIGN PATENT DOCUMENTS

| | | | | |
|---|---|---|---|---|
| WO | WO 91/00048 A2 | | 1/1991 | |
| WO | WO 9100048 A2 | * | 1/1991 | ............ A61B 6/032 |
| WO | WO 9100048 A3 | * | 2/1991 | ............ A61B 6/032 |
| WO | WO 00/75691 A1 | | 12/2000 | |
| WO | WO 2009/060344 A2 | | 5/2009 | |
| WO | WO 2009060344 A2 | * | 5/2009 | ............ A61B 6/032 |
| WO | WO 2009060344 A3 | * | 11/2009 | ............ A61B 6/032 |
| WO | WO 2012/123896 A2 | | 9/2012 | |
| WO | WO 2012123896 A2 | * | 9/2012 | ............ A61B 6/032 |
| WO | WO 2012123896 A3 | * | 11/2012 | ............ A61B 6/032 |

* cited by examiner

DEVICE AND METHOD FOR RADIOGRAPHIC AND NUCLEAR IMAGING OF AN OBJECT

FIELD OF THE INVENTION

A first aspect of the present invention relates to a method for radiographic and nuclear imaging of an object, wherein use is made of a device for radiographic and nuclear imaging of an object by means of x-ray imaging and gamma emission imaging.

BACKGROUND OF THE INVENTION

In WO2012/123896 a device for radiographic and nuclear imaging of an object is disclosed wherein a rotating gantry is provided with opposed first and second support members. An x-ray source is mounted on the first support member and is adapted to emit an x-ray beam in an x-ray beam direction. An x-ray detector is mounted on the second support member and is adapted to image onto the x-ray detector the x-ray beam emitted by the x-ray source in the beam direction.

In WO2012/123896 the rotating gantry is additionally provided with two gamma cameras. Each of the gamma cameras comprises a collimator with one or more collimator openings and each of the gamma cameras further comprises a gamma radiation detector. Further each of the gamma cameras has an associated field of view. The fields of view of the gamma cameras overlap partly, and this overlap defines a focus volume (F) that is seen by the two gamma cameras. The focus volume (F) is located between the x-ray source and the x-ray detector so that the x-ray beam passes through the focus volume (F) and the focus volume (F) is seen by the x-ray detector.

The device disclosed in WO2012/123896 further comprises a computerized image processing unit that is linked to the x-ray detector and is linked to the gamma cameras. This image processing unit is programmed to reconstruct a gamma camera image and is adapted to fuse the gamma camera image with an x-ray image obtained with the x-ray detector into a fused image. The device comprises a display adapted to display an x-ray image, a gamma radiation image, and/or a fused x-ray and gamma radiation image.

In use the gantry of the WO2012/123896 device is in rotation during acquisition of both the x-ray images and the gamma emission images. Thereby a 3-dimensional x-ray image and a 3-dimension emission image are created, which 3-dimensional images can be fused.

The method and device disclosed in WO2012/123896 suffer from an undue complexity both as to the requirements placed on the computerized reconstruction and fusing of the images into a fused image as to the mechanical structure of the device itself.

SUMMARY OF THE INVENTION

According to a first aspect thereof, the present invention provides a method which is characterized in that the support installation is adapted to provide a stationary acquisition position of the x-ray source, x-ray detector, and gamma cameras, during x-ray and gamma image data acquisition of x-ray and gamma radiation images respectively, that are fused into a fused image, and in that the x-ray source, x-ray detector, and gamma cameras are maintained in a stationary acquisition position during x-ray and gamma image data acquisition of x-ray and gamma radiation images respectively, which images are fused into a fused image.

In this method the x-ray equipment and the gamma cameras are held static such that an x-ray image and gamma radiation image, which images are to be fused into a fused image that is to be displayed, are obtained in a fully stationary situation, so without the data acquisition for each image requiring any motion of the x-ray equipment and gamma cameras or parts thereof relative to the object to be examined, e.g. relative to the patient.

In a preferred embodiment the acquisition of the gamma radiation image is performed simultaneous with the acquisition of the x-ray image while x-ray source, x-ray detector, and gamma cameras are held in the stationary acquisition position, e.g. with said gamma radiation image and x-ray image being acquisitioned within at most 1 second. This enhances the fused image quality as both underlying images stem for the same moment in time.

The inventive method allows for an effective fusing of the images into a fused image.

Preferably, the x-ray source is positioned generally between the at least two gamma cameras. For example, the invention can be performed with two gamma cameras, each at opposite sides of the x-ray source, the gamma cameras—also when more than two—basically offering a stereoscopic view by means of their fields of view similar to the eyesight of a human person. Addition of more gamma cameras allows to further enhance the image processing and quality as the focus volume is then seen from even more angles and more positional information becomes available to reconstruct the gamma emission radiation image.

For example, in practical embodiments, a group of multiple gamma cameras, e.g. of 3, 4, 5, or 6 gamma cameras, may be arranged adjacent and distributed around the x-ray source, e.g. in a triangular, square, rectangular, pentagonal, or hexagonal arrangement with the x-ray source generally between the gamma cameras. The x-ray source may be in the geometric center of the group of gamma cameras, but may also be offset relative to the geometric center of the gamma cameras.

Preferably the device is adapted such that the x-ray detector is solely dedicated to x-ray image acquisition.

The method according to the invention may be employed to effectively reconstruct a gamma emission radiation image that is in a plane transverse to the beam direction of the x-ray beam, with the x-ray detector providing an image also in a plane that is transverse to the beam direction. This enhances the fusing of the x-ray image and the gamma emission radiation image into one image. The fused image is preferably reconstructed in real-time, and preferably the image is displayed on a display of the device. This for example allows a medical person performing a medical routine, e.g. a routine involving a catheter, to have an optimal image.

It is envisaged that in an embodiment the gamma cameras are as close as possible to the x-ray source, e.g. with their collimator and/or detector adjoining the x-ray source housing. It is also possible that a spacing is present between the gamma cameras and the x-ray source.

It is preferred for the gamma cameras to be stationary mounted on the first support member and stationary relative to the x-ray source as this allows for a simple construction. In another embodiment the gamma cameras are movably arranged on the first support member, e.g. to allow for setting of a desired static acquisition position of the gamma cameras relative to the object. For example the gamma cameras are mounted on the first support member in a translatable manner in a direction generally parallel to the x-ray beam direction, e.g. on a telescopic arrangement. Possibly the x-ray source is arranged stationary on the first support member whilst the gamma cameras are movable to set the static acquisition position thereof, but in another embodiment also the X-ray source is movable, e.g. to adjust the distance to the opposed x-ray detector to a preferred static acquisition position.

In an embodiment the first free end segment is provided with three gamma cameras, e.g. in a C-arm device with one camera on the left-hand side of the x-ray source, one on the right-hand side, and one at the axial end of the first free end segment of the C-arm beyond the x-ray source.

In a preferred embodiment four gamma cameras are provided on the first support member, e.g. the first free end segment of the C-arm, arranged in two pairs at opposite sides of the x-ray source, so with the x-ray source centered between the gamma cameras.

Whilst even more than four gamma cameras will also be possible, it seems that little effect is achieved by more than four gamma cameras arranged adjacent the x-ray source. However 5 or 6 gamma cameras may also still be practical and an even greater number is not excluded in the invention.

In a preferred embodiment each gamma camera has a pinhole collimator with one or more pinholes, allowing to achieve optimal imaging as is known in the field of gamma cameras.

In an embodiment multiple gamma cameras have a common detector, e.g. embodied as a single planar incident face detector at right angles to the x-ray beam axis that extends along the rear or bottom side of the x-ray source.

In an embodiment the gamma radiation detector of each gamma camera has a planar incident face for said gamma radiation.

In a preferred embodiment the gamma cameras are such that the detectors, or common detector, have (or has) a planar incident faces that is directed perpendicular to the x-ray beam direction.

In an alternative embodiment the gamma cameras have detectors that are arranged at an incline relative to a plane that is normal to the x-ray beam direction such that the incident planes of different camera detectors delimit between them an angle less than 180°. In this embodiment, for example, use may be made of a parallel hole collimator, with a multitude of collimator openings in each collimator, preferably said openings being arranged normal to the incident plane of the underlying detector.

In an embodiment the gamma camera has a pinhole collimator with multiple pinholes, and the camera is provided with a mechanism allowing to select between plural arrangements of one or more pinholes. For example one or more pinhole shutters are envisaged allowing to selectively open or close one or more pinholes to adapted the arrangement of pinholes and thereby the field of view of the respective gamma camera. In another embodiment a mobile pinhole arrangements members is envisaged, having a plurality or different pinhole arrangements, and the mechanism allowing to place a selected pinhole arrangement in working position to define the field of view. In a simple version the collimator of the gamma camera is replaced by another collimator having a different arrangement of one or more pinholes In an embodiment one or more gamma cameras allow for adjustment of the distance between the one or more pinholes of the collimator on the one hand and the detector on the other hand. For example the collimator shield is telescopic to allow for said adjustment.

In an alternative embodiment to a pinhole collimator, each gamma camera has a slant angle collimator with multiple collimator openings arranged at an angle relative to the detector. In another embodiment the collimator is a parallel hole collimator, with the camera's tilted at an angle relative to one another.

In a practically preferred embodiment each gamma camera has a conical radiation shield with a wide base end near the detector and with a narrow apex remote from the detector, the apex being provided with one or more collimator openings, e.g. one or more pinholes.

In a practical embodiment the detectors of the at least two gamma cameras have planar incident faces, e.g. in a common plane.

As is preferred, the x-ray detector is solely adapted to x-ray detection and has no capabilities for imaging gamma emission radiation. However, if desired, a combined gamma ray/x-ray detector could be used.

As is preferred the second support member of the device, e.g. the second free end segment of the C-arm device, is solely provided with a dedicated x-ray detector and is not provided with any gamma camera.

In a practical embodiment, the x-ray source generates a divergent beam of x-rays, e.g. cone beam or fan beam.

In an embodiment the device comprises, possibly in one or more housings distinct and remote from the support installation, computerized image processing unit that is linked to the x-ray detector and to said at least two gamma cameras, the imaging processing unit being programmed to reconstruct a gamma camera image that is intersected by the x-ray beam, or in other words that overlaps with the x-ray field of view of the x-ray equipment.

Preferably the reconstructed gamma radiation image is in a plane transverse to the x-ray beam direction.

Preferably the image processing unit is programmed to fuse an x-ray image with said gamma camera image into a fused image.

Preferably the device comprises a display that is connected to said imaging processing unit and that is adapted to display an x-ray image, a gamma radiation image, and/or a fused x-ray and gamma radiation image, e.g. allowing an operator to switch between said image types as desired.

The first aspect of the invention also relates to a device for radiographic and nuclear imaging of an object by means of x-ray imaging and gamma emission imaging, e.g. of a patient, said device comprising:

a support installation with opposed first and second support members, e.g. a C-arm as described herein, an x-ray source mounted on said first support member and adapted to emit an x-ray beam in an x-ray beam direction, an x-ray detector mounted on said second support member and adapted to image onto said x-ray detector the x-ray beam emitted by said x-ray source in said beam direction, the x-ray detector being solely dedicated to x-ray detection and lacking gamma radiation detection capability, the support installation being adapted to provide a stationary acquisition position of the x-ray source and detector relative to the object during x-ray image data acquisition, wherein the first support member is additionally provided with at least two gamma cameras that are each located adjacent the x-ray source, and wherein each of said at least two gamma cameras comprising a collimator with one or more collimator openings and each of said at least two gamma cameras further comprising a gamma radiation detector, each of said at least two gamma cameras having an associated field of view, wherein the fields of view of said at least two gamma cameras overlap partly, said overlap defining a focus volume that is seen by said at least two gamma cameras, the focus volume being located between the x-ray source and the x-ray detector so that said x-ray beam passes through the focus volume, and wherein the device is adapted to perform acquisition of the gamma radiation image and acquisition of the x-ray image with the gamma cameras also in said stationary acquisition position, wherein the device comprising computerized image processing unit linked to the x-ray detector and to said at least two gamma cameras, the imaging processing unit being programmed to reconstruct a gamma camera image and adapted to fuse said gamma camera image with the obtained x-ray image.

Whilst the first aspect of the invention is described herein predominantly in conjunction with a C-arm device, it is envisaged that the invention can also be applied with other devices having a support installation with opposed first and second support members, an x-ray source mounted on the first support member, and an x-ray detector mounted on the second support member and adapted to image onto said x-ray detector the x-ray beam emitted by said x-ray source. For example the device can be a mammography device or a dedicated thorax device.

For example the support installation, e.g. in a thorax device, may have a vertical column supporting the x-ray detector, e.g. in height adjustable manner, and a further or second support member, e.g. a second vertical column, supporting the x-ray source and gamma cameras, e.g. allowing the patient to stand and/or sit during imaging between the opposed support members. For a mammographic device the support installation may comprise a first breast support member provided with the x-ray detector and a second opposed breast support member provided with the x-ray source and the gamma cameras, preferably at least the distance between said first and second support members being adjustable to adopt to the dimensions of the breast to be examined.

A second aspect of the present invention relates to so-called C-arm devices with have become widely employed in the field of x-ray and/or fluoroscopic examination of patients. In a common design such a C-arm device comprises:
 a C-arm having opposed first and second free end segments,
 a C-arm support structure connected to said C-arm intermediate said first and second free end segments,
 an x-ray source mounted on said first free end segment of the C-arm and adapted to emit an x-ray beam in an x-ray beam direction, and
 an x-ray detector mounted on said second free end segment of the C-arm, so that an x-ray beam emitted by said x-ray source in said beam direction is imaged onto said x-ray detector.

Already in the 1990's it has been proposed to combine x-ray imaging of a patient with gamma emission radiation imaging using a dual mode detector, for example in U.S. Pat. No. 5,155,365.

The integration of this dual mode imaging approach into C-arm devices is for example shown in US2005/0207526. Here the second free end segment of the C-arm is provided with a dual gamma ray/X-ray detector of Cadmium Zinc Telluride (CZT). The same use of a dual mode detector in a C-arm device is shown in US2007/0102645 with reference to FIG. 3 thereof.

Whilst about 20 years have passed since the first proposals for a dual mode detector allowing detection of x-ray and gamma emission radiation for medical imaging, this technology and in particular the integration into C-arm devices has still not seen wide acceptance.

The second aspect of the present invention has as an aim to propose an alternative design of a C-arm device for radiographic and nuclear imaging of an object by means of x-ray and gamma emission imaging.

It is another aim of the second aspect of the invention to provide a C-arm device having a C-arm with opposed first and second free end segments for the x-ray source and the x-ray detector which also has gamma imaging capability and which allows for simultaneous acquisition of x-ray and gamma radiation images in a static imaging position of the relevant parts of the device, so that the images can be effectively fused into a fused image.

It is another aim of the second aspect of the invention to provide a C-arm device allowing for dual mode imaging by means of x-ray and gamma emission radiation imaging.

The second aspect of the invention proposes a C-arm device which comprises—a C-arm having opposed first and second free end segments,
 a C-arm support structure connected to said C-arm intermediate said first and second free end segments,
 an x-ray source mounted on said first free end segment of the C-arm and adapted to emit an x-ray beam in an x-ray beam direction, and
 an x-ray detector mounted on said second free end segment of the C-arm, so that an x-ray beam emitted by said x-ray source in said beam direction is imaged onto said x-ray detector. In the C-arm device the first free end segment of the C-arm is additionally provided with at least two gamma cameras that are each located adjacent the x-ray source. Each of said at least two gamma cameras comprises a collimator with one or more collimator openings and each of said at least two gamma cameras further comprises a gamma radiation detector. Each of said at least two gamma cameras has an associated field of view, and the fields of view of said at least two gamma cameras overlap partly. This overlap defines a focus volume (F) that is seen by said at least two gamma cameras. The focus volume (F) is located between the x-ray source (15) and the x-ray detector so that said x-ray beam passes through the focus volume (F) and the focus volume (F) is seen by the x-ray detector.

The C-arm device allows to achieve dual mode x-ray and gamma radiation imaging without making use of a dual mode detector. This e.g. allows for cost reduction and for enhanced image quality as the x-ray detector can be, and most preferably is, solely dedicated to x-ray detection. For the gamma cameras use can be made of all developments in the field of such gamma cameras.

Preferably, the x-ray source is positioned generally between the at least two gamma cameras. For example, the C-arm device can be equipped with two gamma cameras, each at opposite sides of the x-ray source, the gamma cameras—also when more than two—basically offering a stereoscopic view by means of their fields of view similar to the eyesight of a human person. Addition of more gamma cameras allows to further enhance the image processing and quality as the focus volume is then seen from even more angles and more positional information becomes available to reconstruct the gamma emission radiation image.

For example, in practical embodiments, a group of multiple gamma cameras, e.g. of 3, 4, 5, or 6 gamma cameras, may be arranged adjacent and distributed around the x-ray source, e.g. in a triangular, square, rectangular, pentagonal, or hexagonal arrangement with the x-ray source generally between the gamma cameras. The x-ray source may be in the geometric center of the group of gamma cameras, but may also be offset relative to the geometric center of the gamma cameras.

Preferably the support installation is adapted to provide a stationary acquisition position of the x-ray equipment and gamma cameras during x-ray and gamma image data acquisition in the course of establishing x-ray and gamma radiation images respectively. Preferably images that are to be fused into a fused image are acquisitioned from a single stationary acquisition position of the x-ray equipment and the gamma cameras.

Preferably the C-arm device is embodied to perform acquisition of the gamma radiation image simultaneous with the acquisition of the x-ray image while the x-ray equipment and gamma cameras are in a stationary acquisition position.

Preferably the C-arm device is adapted such that the x-ray detector is solely dedicated to x-ray image acquisition.

The C-arm device may be employed to effectively reconstruct a gamma emission radiation image that is in a plane transverse to the beam direction of the x-ray beam, with the x-ray detector providing an image also in a plane that is transverse to the beam direction. This enhances the fusing of the x-ray image and the gamma emission radiation image into one image. The fused image is preferably reconstructed in real-time, and preferably the image is displayed on a display of the device. This for example allows a medical person performing a medical routine, e.g. a routine involving a catheter, to have an optimal image.

In an embodiment the C-arm device allows to simultaneously obtain an x-ray image and gamma radiation image that are to be fused into a fused image, e.g. with both images being acquisitioned within at most 1 second. This enhances the fused image quality as both underlying images stem for the same moment in time.

Preferably the x-ray equipment and the gamma cameras are embodied such that an x-ray image and gamma radiation image that are to be fused into a fused image that is to be displayed, can be obtained in a fully stationary situation, so without the data acquisition for each image requiring any motion of the x-ray equipment and gamma cameras or parts thereof relative to the object to be examined, e.g. relative to the patient.

It is envisaged that in an embodiment the gamma cameras are as close as possible to the x-ray source, e.g. with their collimator and/or detector adjoining the x-ray source housing. It is also possible that a spacing is present between the gamma cameras and the x-ray source.

It is preferred for the gamma cameras to be stationary mounted on the first free end segment and stationary relative to the x-ray source as this allows for a simple construction.

In another embodiment the gamma cameras are movably arranged on the first free end segment, e.g. to allow for setting of a desired static acquisition position of the gamma cameras relative to the object. For example the gamma cameras are mounted on the first free end segment in a translatable manner in a direction generally parallel to the x-ray beam direction, e.g. on a telescopic arrangement. Possibly the x-ray source is arranged stationary on the first free end segment whilst the gamma cameras are movable to set the static acquisition position thereof, but in another embodiment also the X-ray source is movable, e.g. to adjust the distance to the opposed x-ray detector to a preferred static acquisition position.

In an embodiment the first free end segment is provided with three gamma cameras, e.g. in a C-arm device with one camera on the left-hand side of the x-ray source, one on the right-hand side, and one at the axial end of the first free end segment of the C-arm beyond the x-ray source.

In a most preferred embodiment four gamma cameras are provided on the first free end segment of the C-arm, arranged in two pairs at opposite sides of the x-ray source, so with the x-ray source centered between the gamma cameras.

Whilst even more than four gamma cameras will also be possible, it seems that little effect is achieved by more than four gamma cameras arranged adjacent the x-ray source. However 5 or 6 gamma cameras may also still be practical and an even greater number is not excluded in the invention.

In a preferred embodiment each gamma camera has a pinhole collimator with one or more pinholes, allowing to achieve optimal imaging as is known in the field of gamma cameras.

In an embodiment multiple cameras have a common detector, e.g. embodied as a single planar incident face detector at right angles to the x-ray beam axis that extends along the rear or bottom side of the x-ray source.

In an embodiment the gamma radiation detector of each gamma camera has a planar incident face for said gamma radiation.

In a preferred embodiment the gamma cameras are such that the detectors, or common detector, have (or has) a planar incident faces that is directed perpendicular to the x-ray beam direction.

In an alternative embodiment the gamma cameras have detectors that are arranged at an incline relative to a plane that is normal to the x-ray beam direction such that the incident planes of different camera detectors delimit between them an angle less than 180°. In this embodiment, for example, use may be made of a parallel hole collimator, with a multitude of collimator openings in each collimator, preferably said openings being arranged normal to the incident plane of the underlying detector.

In an embodiment the gamma camera has a pinhole collimator with multiple pinholes, and the camera is provided with a mechanism allowing to select between plural arrangements of one or more pinholes. For example one or more pinhole shutters are envisaged allowing to selectively open or close one or more pinholes to adapted the arrangement of pinholes and thereby the field of view of the respective gamma camera. In another embodiment a mobile pinhole arrangements members is envisaged, having a plurality or different pinhole arrangements, and the mechanism allowing to place a selected pinhole arrangement in working position to define the field of view. In a simple version the collimator of the gamma camera is replaced by another collimator having a different arrangement of one or more pinholes In an embodiment one or more gamma cameras allow for adjustment of the distance between the one or more pinholes of the collimator on the one hand and the detector on the other hand. For example the collimator shield is telescopic to allow for said adjustment.

In an alternative embodiment to a pinhole collimator, each gamma camera has a slant angle collimator with multiple collimator openings arranged at an angle relative to the detector. In another embodiment the collimator is a parallel hole collimator, with the camera's tilted at an angle relative to one another.

In a practically preferred embodiment each gamma camera has a conical radiation shield with a wide base end near the detector and with a narrow apex remote from the detector, the apex being provided with one or more collimator openings, e.g. one or more pinholes.

In a practical embodiment the detectors of the at least two gamma cameras have planar incident faces, e.g. in a common plane.

As is preferred, the x-ray detector is solely adapted to x-ray detection and has no capabilities for imaging gamma emission radiation. However, if desired, a combined gamma ray/x-ray detector could be used.

As is preferred the second free end segment of the C-arm device, is solely provided with a dedicated x-ray detector and is not provided with any gamma camera.

In a practical embodiment, the x-ray source generates a divergent beam of x-rays, e.g. cone beam or fan beam.

In an embodiment the C-arm device comprises, possibly in one or more housings distinct and remote from the support installation, computerized image processing unit that is linked to the x-ray detector and to said at least two gamma cameras, the imaging processing unit being programmed to reconstruct a gamma camera image that is intersected by the x-ray beam, or in other words that overlaps with the x-ray field of view of the x-ray equipment. Preferably the reconstructed gamma radiation image is in a plane transverse to the x-ray beam direction.

Preferably the image processing unit is programmed to fuse an x-ray image with said gamma camera image into a fused image.

Preferably the device comprises a display that is connected to said imaging processing unit and that is adapted to display an x-ray image, a gamma radiation image, and/or a fused x-ray and gamma radiation image, e.g. allowing an operator to switch between said image types as desired.

The second aspect of the invention can be effected by means of conversion of a pre-assembled, commonly an already operational, x-ray dedicated C-arm device into a dual mode imaging device, by mounting onto the x-ray source carrying first free end segment an assembly of at least two gamma cameras so that they are each located adjacent the x-ray source,
each of said at least two gamma cameras comprising a collimator with one or more collimator opening and further comprising a gamma radiation detector, each of said at least two gamma cameras having an associated field of view,
the fields of view of said at least two gamma cameras overlapping partly, said overlap defining a focus volume that is seen by said at least two gamma cameras, the focus volume being located between the x-ray source and the x-ray detector so that said x-ray beam passes through the focus volume and the focus volume is seen by the x-ray detector.

The second aspect of the invention also relates to a method for such a conversion and to a conversion assembly comprising said at least two gamma cameras, which conversion assembly is adapted to be mounted onto an x-ray source carrying free end segment of a C-arm device.

It is envisaged that a C-arm device manufacturer can provide such conversion assemblies tailored to their ordinary, x-ray dedicate C-arm devices and offer such assemblies e.g. to hospitals to enhance the imaging capabilities of their C-arm device. Preferably such assembly is embodied such that the x-ray source is left as it is without any changes, at most a protective shell being removed and replaced by another shell to accommodate for the conversion assembly or the assembly being housed in a common shell with the x-ray source.

A third aspect of the invention relates to a device for radiographic and nuclear imaging of an object by means of x-ray imaging and gamma emission imaging, the device comprising:
- a support installation with opposed first and second support members,
- an x-ray source mounted on the first support member and adapted to emit an x-ray beam in an x-ray beam direction,
- an x-ray detector mounted on the second support member and adapted to image onto said x-ray detector the x-ray beam emitted by said x-ray source in said beam direction, which device is characterized in that the first support member of the support installation is additionally provided with at least two gamma cameras that are each located adjacent the x-ray source, and in that each of said at least two gamma cameras comprises a collimator with one or more collimator openings and each of said at least two gamma cameras further comprising a gamma radiation detector, each of said at least two gamma cameras having an associated field of view, and in that the fields of view of said at least two gamma cameras overlap partly, said overlap defining a focus volume that is seen by said at least two gamma cameras, the focus volume being located between the x-ray source and the x-ray detector so that said x-ray beam passes through the focus volume and the focus volume is seen by the x-ray detector.

The inventive device according to the third aspect of the invention allows to achieve dual mode x-ray and gamma radiation imaging without making use of a dual mode detector. This e.g. allows for cost reduction and for enhanced image quality as the x-ray detector can be, and most preferably is, solely dedicated to x-ray detection. For the gamma cameras use can be made of all developments in the field of such gamma cameras.

Preferably, the x-ray source is positioned generally between the at least two gamma cameras. For example, the invention can be performed with two gamma cameras, each at opposite sides of the x-ray source, the gamma cameras—also when more than two—basically offering a stereoscopic view by means of their fields of view similar to the eyesight of a human person. Addition of more gamma cameras allows to further enhance the image processing and quality as the focus volume is then seen from even more angles and more positional information becomes available to reconstruct the gamma emission radiation image.

The device according to the third aspect of the invention may have one or more of the features discussed with reference to the device of the first and/or second aspect of the invention.

The invention also relates to a method for radiographic and nuclear imaging an object, e.g. a body of a patient, wherein use is made of the inventive device.

The aspects of the present invention will now be explained with reference to the drawings.

DETAILED DESCRIPTION OF EMBODIMENTS

Figure 1:
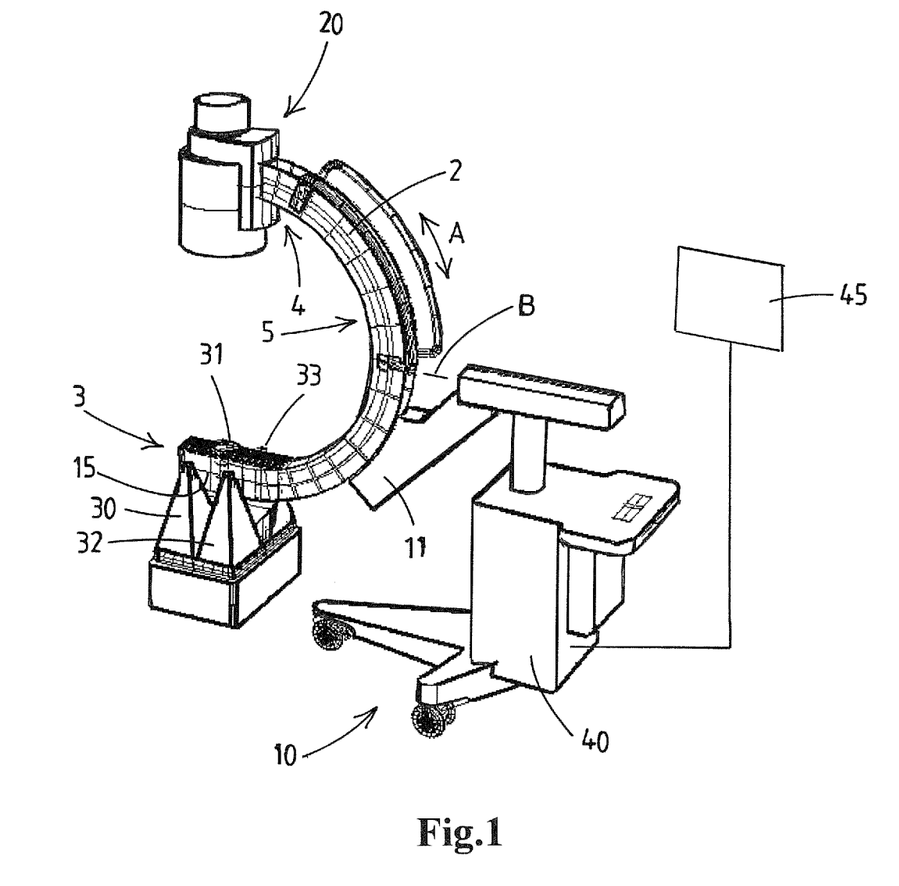
FIG. 1 shows in perspective view, schematically, an example of a device according to the invention for radiographic and nuclear imaging of an object by means of x-ray and gamma emission imaging, e.g. of a patient.
Figure 2:
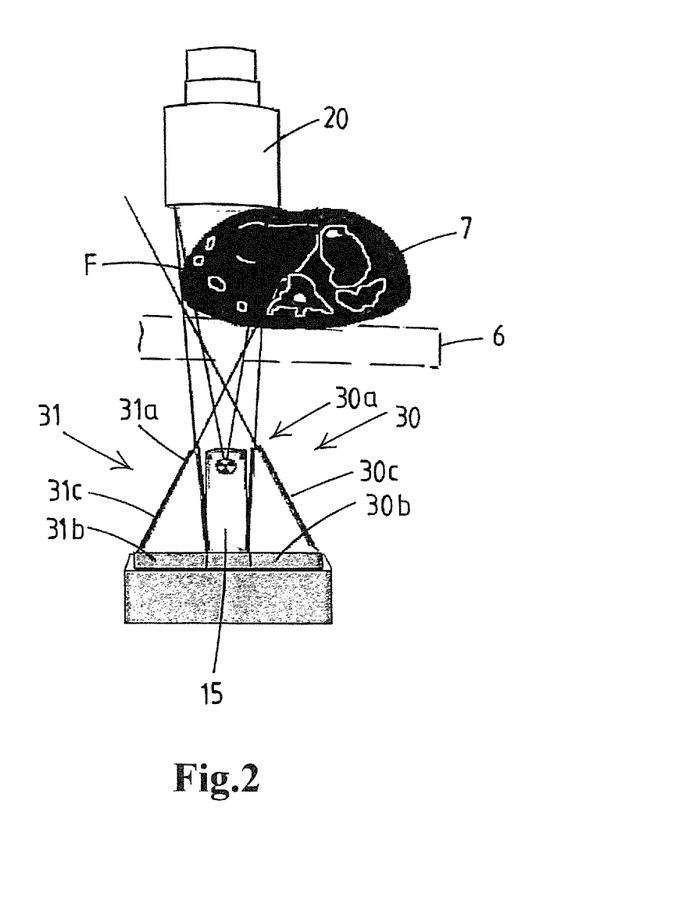
FIG. 2 shows schematically, in a cross-sectional view on the free end segments of the C-arm, the device of FIG. 1, a part of a patient, an a patient support table.
Figure 3:
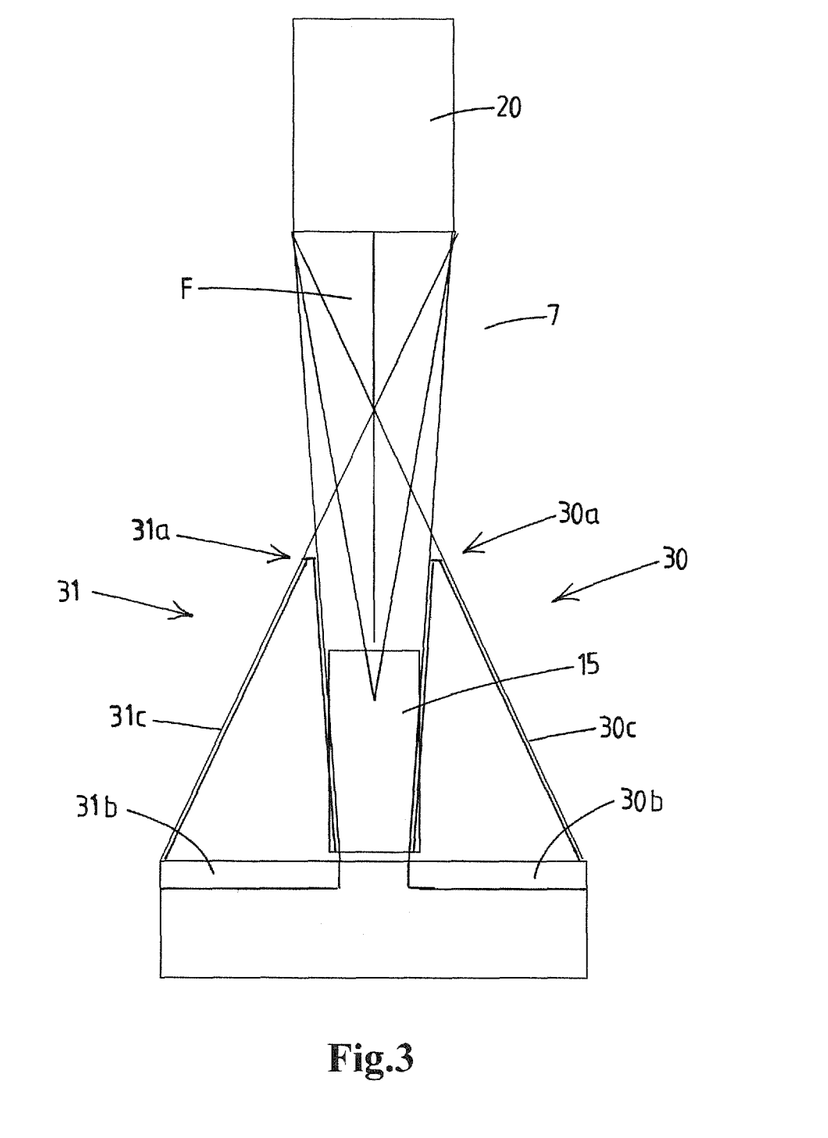
FIG. 3 shows diagrammatically the arrangement of relevant parts of the device in a view according to FIG. 2.
Figure 4A:
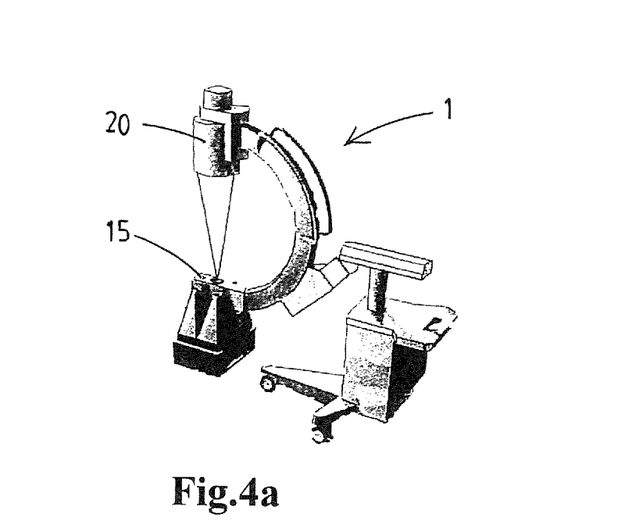
FIG. 4a shows the device of FIG. 1 with conical x-ray beam.
Figure 4B:
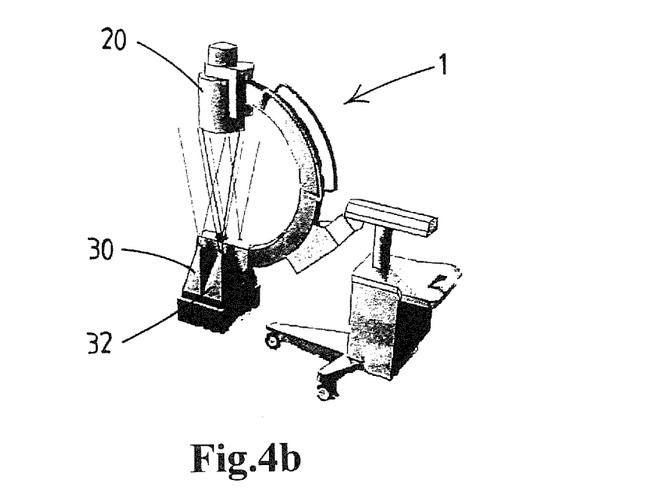
FIG. 4b shows the device of FIG. 1 with the fields of view of the gamma cameras.

With reference to FIGS. 1-4 an exemplary embodiment of a device 1 for radiographic and nuclear imaging of a patient or other object by means of x-ray and gamma emission imaging will be discussed. The FIGS. 1 and 4 show an operator of the device.

The device 1 is a C-arm device comprising a C-arm 2 having a first free end segment 3, a second free end segment 4 opposite from the segment 3, and an intermediate segment 5 that interconnects the first and second free end segments 3, 4. Between the segments 3 and 4 there is an opening space allowing e.g. to place the device in lateral direction over a patient table 6 upon which a patient 7 is lying (see FIG. 2). Here, as is common and preferred in C-arm devices, the intermediate segment is an arctuate segment of uniform radius.

The device 1 further comprises a C-arm support structure 10 that is connected to said C-arm, here between said first and second free end segments, here to the arctuate intermediate segment 5. As is preferred, the support structure allows to rotate the C-arm about an axis that is perpendicular to the plane of the C-arm as a connector member 11 that engages onto the C-arm allows the arctuate segment to slide there along over a limited angular range, the motion being indicated with arrow A in FIG. 1.

Possibly, and preferably, the structure 10 also defines an axis of rotation of the C-arm that lies in the plane of the C-arm, preferably a horizontal axis defined by to the support structure 10, here indicated as axis B.

The support structure 10 can be embodied as a wheeled structure so as to allow for travel over a floor, but other embodiments are also possible, e.g. rail mounted, ceiling mounted, wall mounted, fixed mounting on a floor, etc.

An x-ray source 15 is mounted on the first free end segment 3 of the C-arm 2. Commonly this x-ray source will include an x-ray tube, and possibly a shutter device allowing to interrupt the x-ray beam emitted by the x-ray source.

An x-ray detector 20, here as is preferred an x-ray detector dedicated to x-ray, is mounted on said second free end segment of the C-arm, so that an x-ray beam emitted by the x-ray source in a beam direction is imaged onto the x-ray detector 20.

As can be seen in the FIGS. 1-4 the first free end segment 3 of the C-arm 2 is additionally provided with at least two gamma cameras 30, 31 that are each located adjacent the x-ray source 15 with the x-ray source 15 positioned between the at least two gamma cameras 31, 32.

In this example, as is preferred, four gamma cameras 30, 31, 32, 33, are provided on the first free end segment 3 of the C-arm 2, arranged two pairs of gamma cameras at opposite sides of the x-ray source 15. Here the arrangement is a in square with the x-ray source in the center, but other spatial arrangements, possibly with another number of gamma cameras are also possible.

Each of the gamma cameras 30-33 has a collimator 30a-33a with one or more collimator openings and each of the gamma cameras 30-33 further comprises a gamma radiation detector 30b-33b.

Each gamma camera 30-33 has an associated field of view, which is schematically shown in FIGS. 2, 3 and 4b.

As can be seen in FIG. 2 the x-ray source 15 lies fully outside the field of view of each of the gamma cameras 30-33.

The fields of view the overlapping partly, in this example as is preferred, each field of view has some overlap with all other fields of view of the other gamma cameras. The overlap defines a focus volume F that is seen by at least two, and here as is preferred all, gamma cameras 30-33.

The focus volume F is located between the x-ray source 15 and the x-ray detector 20 so that the x-ray beam passes through the focus volume F and the focus volume F is seen by the x-ray detector.

As explained above this arrangement allows to construct a gamma emission radiation image that is in a plane parallel to the imaging plane of the x-ray system, which is perpendicular to the beam direction of the x-ray beam.

As is preferred, the x-ray beam is a conical beam (see FIG. 4a), but other beam embodiments, e.g. a fanned beam, are also possible.

In the FIGS. 1-4 it is illustrated that each gamma camera 30-33 has a conical radiation shield 30c-33c with a wide base end near the detector 30ba-33b and with a narrow apex remote from the detector. The apex is embodied as collimator with one or more collimator openings, here is preferred with a single pinhole or a group or cluster of pinholes.

Figure 5:
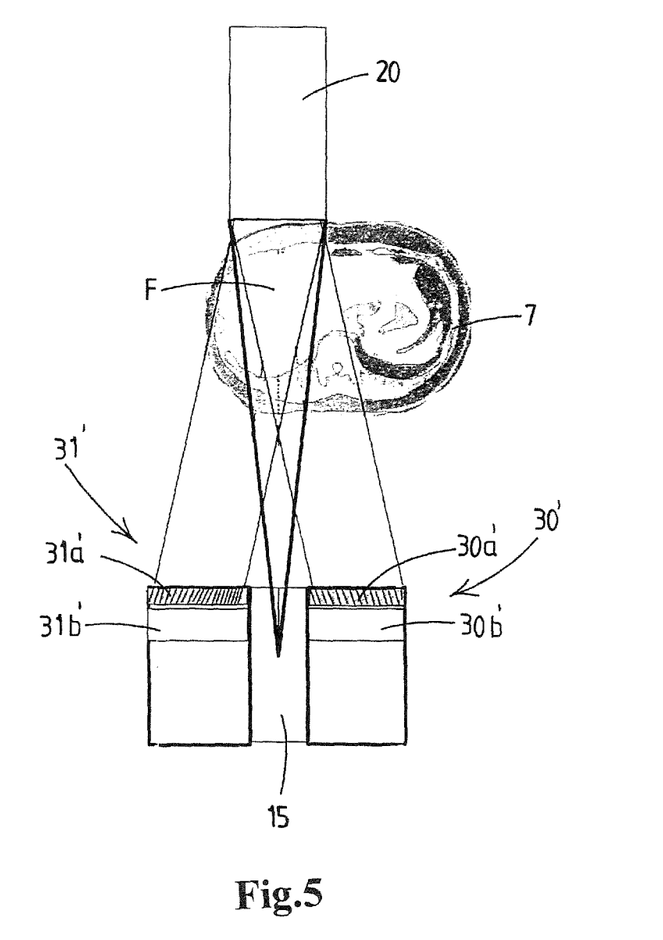
FIG. 5 shows schematically, in a view corresponding to FIG. 3, an alternative device using slant angle collimator type cameras.

FIG. 5 illustrates an alternative version wherein the gamma cameras 30'-33' are not provided with the conical shield and pinhole collimator, but are provided with a slant angle collimator 33a' with multiple collimator openings arranged at an angle relative to the detector 30b'. This also leads to each camera having its own field of view and the fields of view overlapping partly in a focus volume F that is intersected by the x-ray beam.

The device comprises computerized image processing unit 40 that linked to the x-ray detector 15 and to the gamma cameras 30-33. This imaging processing unit 40 is programmed to reconstruct a gamma camera image in a plane transverse to the x-ray beam direction on the basis of the information received from the detectors 30b-33b.

As is preferred unit is programmed to fuse an x-ray image with the image obtained by means of the gamma cameras.

The device may be embodied to alternate the x-ray imaging with gamma emission imaging, e.g. by means of a pulsed x-ray beam and the gamma imaging being effected in the pauses between x-ray pulses. Other approaches are also possible.

Preferably the device 1 comprises a display 45 adapted to display an x-ray image, a gamma radiation image, and/or a fused x-ray and gamma radiation image.

The skilled person will appreciate that the cameras 30-33 can be embodied as a gamma camera assembly that is adapted to be mounted on the first free end segment 3 of a C-arm 2 that is provided with an x-ray source 15, e.g. in view of retrofitting such an assembly on an existing x-ray C-arm device in order to achieve dual mode imaging capability.

Figure 6:
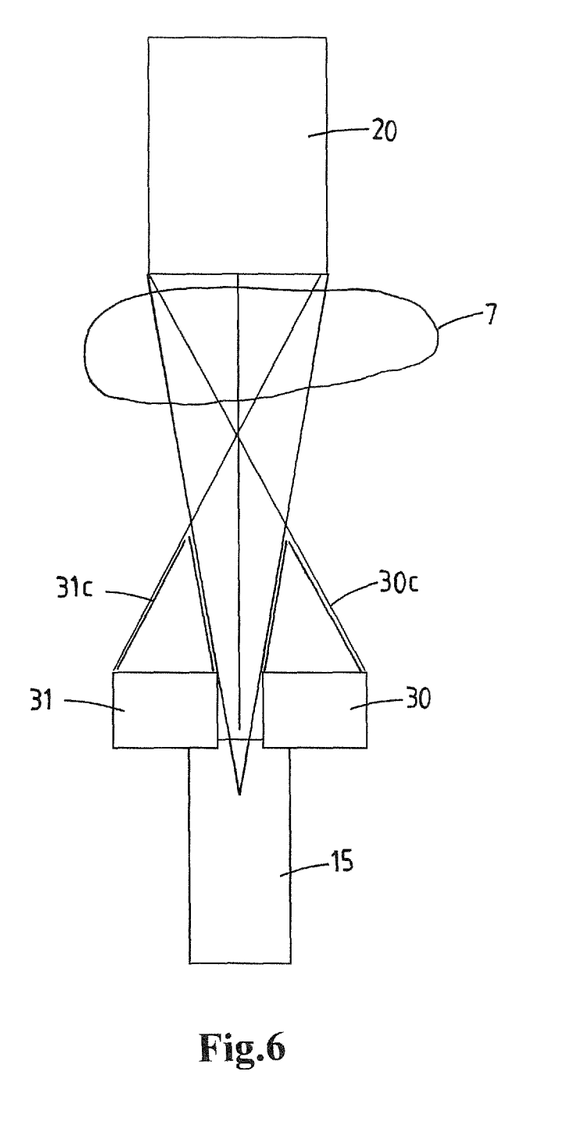
FIG. 6 shows schematically, in a view corresponding to FIG. 4, an alternative arrangement of the gamma cameras.

FIG. 6 illustrates an alternative wherein the cameras 30-33 are mounted higher relative to the x-ray source 15 than in FIG. 1. The shields 30c-33c extend upward beyond the top end of the x-ray source 15. As in FIGS. 1-4 and in FIG. 5, the x-ray source 15 is located between the cameras 30-33 and the x-ray beam (which here also is conical) is not interfering with the shields 30c-33c of the gamma cameras. This arrangement achieves the effect that the gamma cameras 30-33 can be closer to the patient 7 yet at the expense of reduction of the free space between the opposed end segments of the C-arm device.

Figure 7:
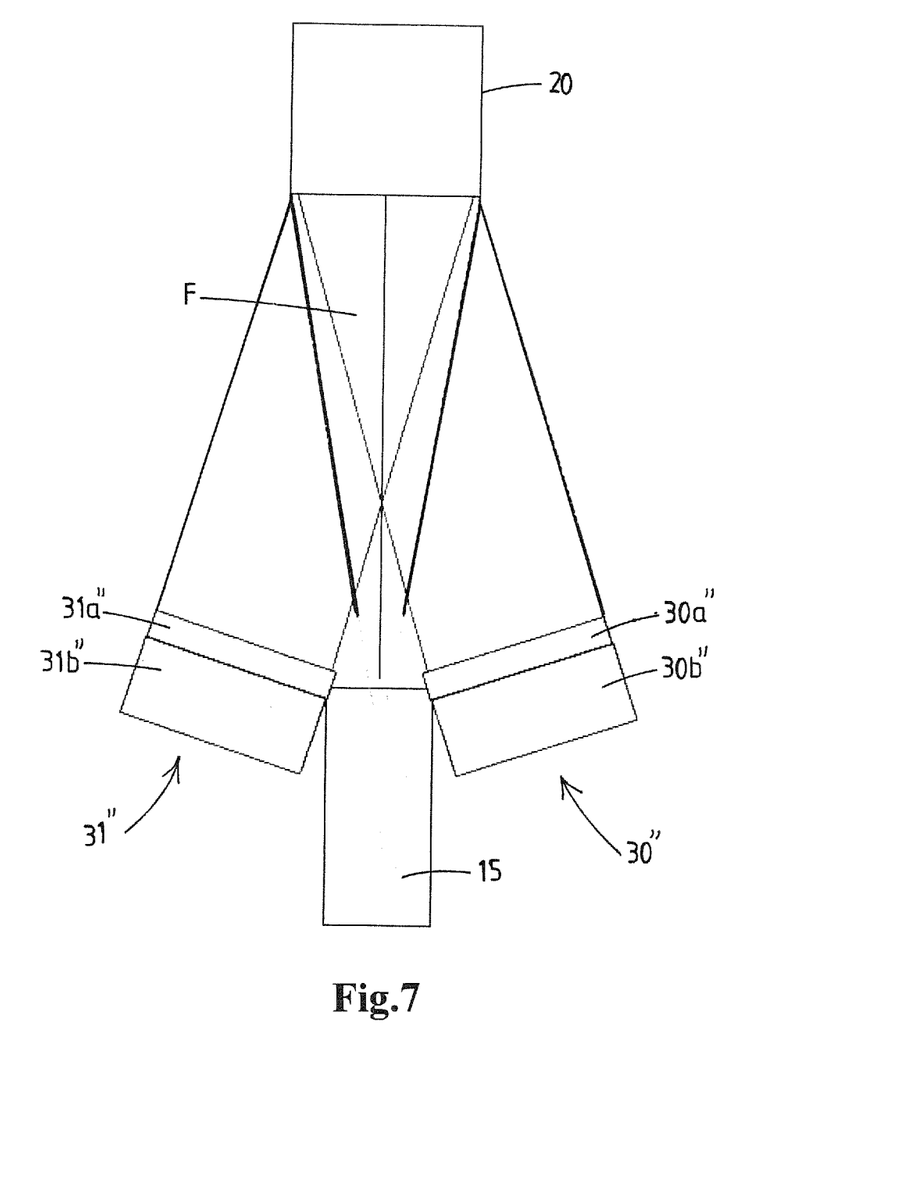
FIG. 7 shows schematically, in a view corresponding to FIG. 3, an alternative device using parallel hole collimator type cameras.

FIG. 7 illustrates a further alternative version wherein the gamma cameras 30"-31" are provided with a parallel hole collimator 30a", 31a" with multiple collimator openings arranged normal to the planar incident face of the underlying detector 30b", 31b". This also leads to each camera having its own field of view and the fields of view overlapping partly in a focus volume F that is intersected by the x-ray beam. As can be seen the detectors 30b", 31b" are arranged at an incline relative to a plane that is normal to the x-ray beam direction such that the incident planes of different gamma camera detectors delimit between them an angle less than 180°.

Figure 8:
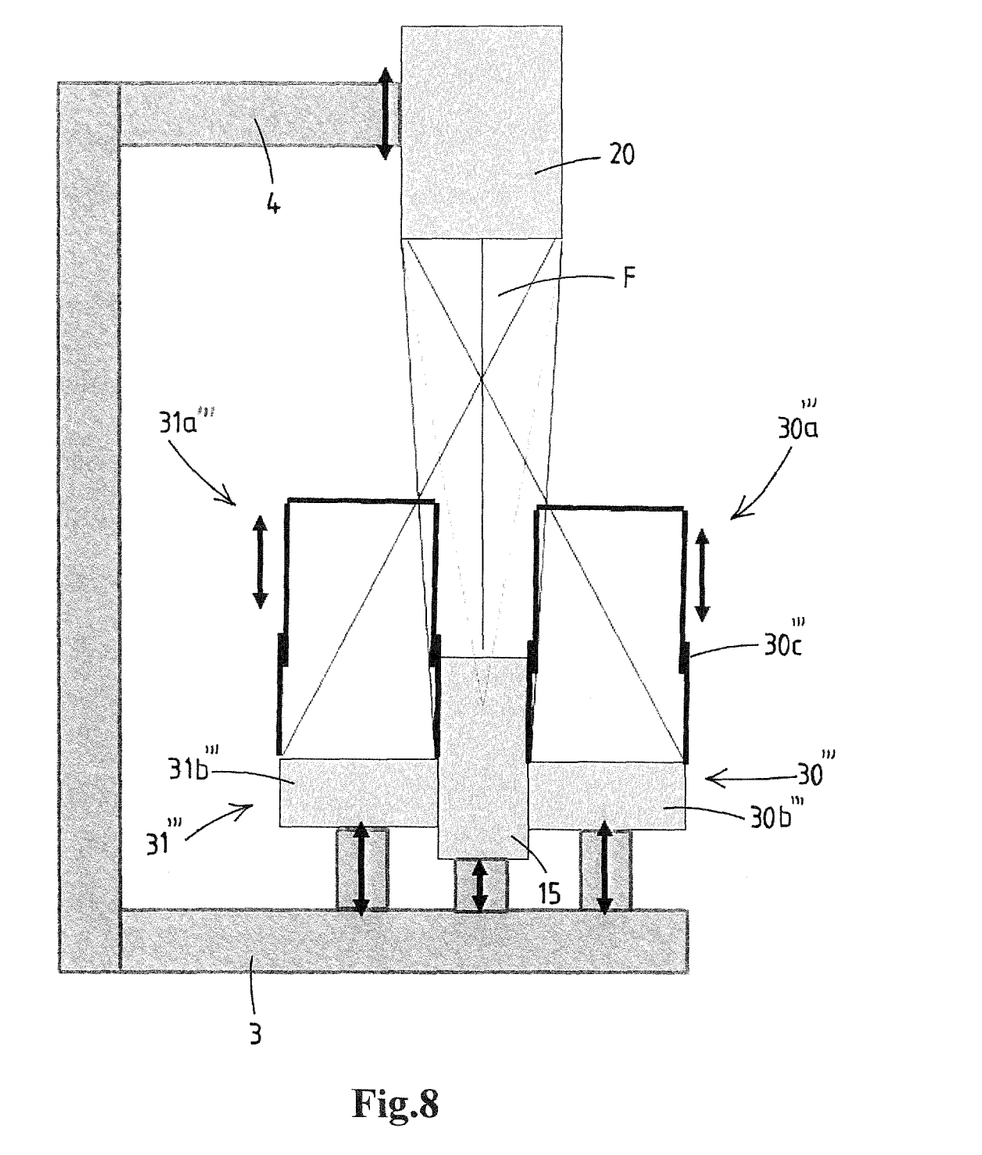
FIG. 8 shows schematically another example of a device according to the invention.

FIG. 8 illustrates schematically an embodiment that allows the operator to adjust and set the stationary acquisition position of the x-ray equipment and the gamma cameras, e.g. dependent on the object to be examined, e.g. the patient.

It is illustrated that the gamma cameras 30'" and 31'" are movably arranged on the first support member 3 to allow for setting of a desired static acquisition position of the gamma cameras relative to the object. The gamma cameras are mounted on the first support member in a translatable manner in a direction generally parallel to the x-ray beam direction, e.g. on a telescopic arrangement as indicated with arrows. In this example also the x-ray source 15 is movable mounted on the support member 3, also in a translatable manner in a direction generally parallel to the x-ray beam direction, e.g. on a telescopic arrangement as indicated with an arrow. In this example it is illustrated that, if desired, also the x-ray detector 20 can be movably mounted on the second support member, e.g. in a translatable manner in a direction generally parallel to the x-ray beam direction, e.g. on a telescopic arrangement as indicated with an arrow.

As explained, the adjustability of the static acquisition position of the gamma cameras and/or of the x-ray source, and/or of the x-ray detector, e.g. in translatory manner towards and away from the opposite support member of the installation, may be used to achieve an optimal position relative to the object to be imaged.

It is noted that the device of FIG. 8 could, for example, be a C-arm device with the first and second support members 3, 4 interconnected by a C-arm. In another embodiment, the first and second support members 3, 4, could for example be vertical support columns (so that the FIG. 8 is a top view), e.g. for a patient standing in the space between the x-ray source and detector.

FIG. 8 also illustrates the provision of one or more gamma cameras 30'" and 31'" that allows for adjustment of the distance between the one or more pinholes of the collimator 30a'" and 31a'" on the one hand and the detector 30b'" and 31b'" on the other hand. In this example the collimator shield 30c'" and 31c'" is telescopic to allow for said adjustment, e.g. with a motor drive to effect the telescopic motion as depicted with arrows. It will be appreciated that the possibility for adjustment of the distance between the one or more pinholes and the detector can also be employed in devices wherein the gamma cameras and/or x-ray source and/or x-ray detector are stationary mounted on their respective support member. It will further be appreciated that the distance adjustment possibility may allow for variation of the overlap of the fields of view of the gamma cameras, or simply to provide for a retracted mode of the gamma cameras for situations wherein the gamma cameras are not used, e.g. to create maximum space for the object and object support, e.g. a patient support table.

The invention claimed is:

1. A method for radiographic and nuclear imaging an object, wherein use is made of a C-arm device for radiographic and nuclear imaging of an object by means of x-ray imaging and gamma emission imaging, said C-arm device comprising:
    a C-arm with opposed first and second free end segments,
    an x-ray source mounted on said first free end segment and adapted to emit an x-ray beam in an x-ray beam direction,
    an x-ray detector mounted on said second free end segment and adapted to image onto said x-ray detector the x-ray beam emitted by said x-ray source in said beam direction,
    wherein the first free end segment of the C-arm is additionally provided with at least two gamma cameras that are each located adjacent the x-ray source,
    wherein each of said at least two gamma cameras comprises a collimator with one or more collimator openings and each of said at least two gamma cameras further comprises a gamma radiation detector,
    wherein each of said at least two gamma cameras has an associated field of view,
    wherein the fields of view of said at least two gamma cameras overlap partly, said overlap defining a focus volume that is seen by said at least two gamma cameras, the focus volume being located between the x-ray source and the x-ray detector so that said x-ray beam passes through the focus volume and the focus volume is seen by the x-ray detector,
    wherein the C-arm device comprises a computerized image processing unit linked to the x-ray detector and linked to said at least two gamma cameras, the imaging processing unit being programmed to reconstruct a gamma camera image and being adapted to fuse said gamma camera image with an x-ray image obtained with the x-ray detector into a fused image,
    wherein the C-arm device comprises a display adapted to display an x-ray image, a gamma radiation image, and/or a fused x-ray and gamma radiation image,
    wherein the C-arm is adapted to provide a stationary acquisition position of the x-ray source, x-ray detector, and gamma cameras, during x-ray and gamma image data acquisition of x-ray and gamma radiation images respectively, that are fused into a fused image, and
    wherein the x-ray source, x-ray detector, and gamma cameras are maintained in a stationary acquisition position during x-ray and gamma image data acquisition of x-ray and gamma radiation images respectively, which images are fused into a fused image.

2. The method according to claim 1, wherein acquisition of the gamma radiation image is performed simultaneous with the acquisition of the x-ray image while x-ray source, x-ray detector, and gamma cameras are held in said stationary acquisition position.

3. The method according to claim 1, wherein the x-ray source is positioned generally between said at least two gamma cameras.

4. The method according to claim 3, wherein four gamma cameras are provided on the first free end segment, arranged in two pairs of gamma cameras at opposite sides of the x-ray source.

5. The method according to claim 1, wherein each gamma camera has a pinhole collimator with one or more pinholes.

6. The method according to claim 5, wherein each gamma camera has a conical radiation shield with a wide base end near the detector and with a narrow apex remote from the detector, the apex being provided with a one or more pinholes.

7. The method according to claim 1, wherein each gamma camera has a slant angle collimator with multiple collimator openings arranged at an angle relative to the detector.

8. The method according to claim 1, wherein the C-arm device is adapted such that the x-ray detector is solely dedicated to x-ray image acquisition.

9. A C-arm device comprising:
a C-arm having opposed first and second free end segments,
a C-arm support structure connected to said C-arm intermediate said first and second free end segments,
an x-ray source mounted on said first free end segment of the C-arm and adapted to emit an x-ray beam in an x-ray beam direction, and
an x-ray detector mounted on said second free end segment of the C-arm, so that an x-ray beam emitted by said x-ray source in said beam direction is imaged onto said x-ray detector,
wherein
the first free end segment of the C-arm is additionally provided with at least two gamma cameras that are each located adjacent the x-ray source,
each of said at least two gamma cameras comprising a collimator with one or more collimator openings and each of said at least two gamma cameras further comprising a gamma radiation detector,
each of said at least two gamma cameras having an associated field of view,
the fields of view of said at least two gamma cameras overlapping partly, said overlap defining a focus volume that is seen by said at least two gamma cameras, the focus volume being located between the x-ray source and the x-ray detector so that said x-ray beam passes through the focus volume and the focus volume is seen by the x-ray detector.

10. A gamma camera assembly adapted to be mounted on a first free end segment of a C-arm of a C-arm device, which C-arm is provided with an x-ray source on the first free end segment and with an x-ray detector on an opposed second free end segment, which assembly comprises at least two gamma cameras that are arranged to be each located adjacent the x-ray source,
each of said at least two gamma cameras comprising a collimator with one or more collimator opening and further comprising a gamma radiation detector, each of said at least two gamma cameras having an associated field of view,
the fields of view of said at least two gamma cameras overlapping partly, said overlap defining a focus volume that is seen by said at least two gamma cameras, the focus volume being located between the x-ray source and the x-ray detector so that said x-ray beam passes through the focus volume and the focus volume is seen by the x-ray detector of the C-arm device.

11. A method for the conversion of a pre-assembled x-ray dedicated C-arm device into a dual mode imaging device, said device comprising:
a C-arm having opposed first and second free end segments,
a C-arm support structure connected to said C-arm,
an x-ray source mounted on said first free end segment of the C-arm,
an x-ray detector mounted on said second free end segment of the C-arm, so that an x-ray beam emitted by said x-ray source in a beam direction is imaged onto said x-ray detector, the x-ray detector being solely dedicated to x-ray detection and lacking gamma radiation detection capability,
wherein the method comprises
mounting onto the first free end segment of said C-arm, onto which the x-ray source has been pre-mounted, an assembly of at least two gamma cameras so that they are each located adjacent the x-ray source,
each of said at least two gamma cameras comprising a collimator with one or more collimator openings and further comprising a gamma radiation detector, each of said at least two gamma cameras having an associated field of view,
the fields of view of said at least two gamma cameras overlapping partly, said overlap defining a focus volume that is seen by said at least two gamma cameras, the focus volume being located between the x-ray source and the x-ray detector so that said x-ray beam passes through the focus volume and the focus volume is seen by the x-ray detector.

12. The method according to claim 2, wherein said gamma radiation image and x-ray image are acquisitioned within at most 1 second.

* * * * *